United States Patent
Hellinga

(10) Patent No.: US 6,521,446 B2
(45) Date of Patent: Feb. 18, 2003

(54) BIOSENSOR

(75) Inventor: Homme W. Hellinga, Durham, NC (US)

(73) Assignee: Duke University, Durham, NC (US)

( * ) Notice: Subject to any disclaimer, the term of this patent is extended or adjusted under 35 U.S.C. 154(b) by 0 days.

(21) Appl. No.: 09/891,307

(22) Filed: Jun. 27, 2001

(65) Prior Publication Data

US 2002/0004217 A1 Jan. 10, 2002

Related U.S. Application Data

(62) Division of application No. 09/223,775, filed on Dec. 31, 1998, now Pat. No. 6,277,627.
(60) Provisional application No. 60/070,293, filed on Dec. 31, 1997.

(51) Int. Cl.$^7$ .............................................. G01N 33/66
(52) U.S. Cl. ........................ 435/287.1; 435/7.2; 435/14; 435/172.1; 435/287.2; 435/288.7; 435/808; 435/817; 436/172; 436/518; 436/805
(58) Field of Search ................................ 204/400, 403; 422/82.05, 82.08; 435/7.2, 14, 172.1, 287.1, 287.2, 288.7, 808, 817; 436/172, 518, 805

(56) References Cited

PUBLICATIONS

Li et al, "Comparative stereochemical analysis of glucose–binding proteins for rational design of glucose–specific agents", J. Biomater. Sci. Polymer Edn, 9(4):327–344 (1998).
Wilkins and Atanasov, "Glucose monitoring: state of the art and future possibilities", Med. Eng. Phys. 18(4):273–288 (1996).
Pickup, "Developing glucose sensors for n vivo use", Trends in Biochech. 11:285–291 (1993).
Marvin et al, "The rational design of allosteric interactions in a monomeric protein and its applications to the construction of biosensors", Proc. Natl. Acad. Sci. USA 94:4366–4371 (1997).
Brune et al, "Direct, Real–Time Measurement of Rapid Inorganic Phosphate Release Using a Novel Fluorescent Probe and Its Application to Actomyosin Subfragment 1 ATPase", Biochemistry 33(27):8262–8271 (1994).
Marvin and Hellinga, "Engineering Biosensors by Introducing Fluorescent Allosteric Signal Transducers: Construction of a Novel Glucose Sensor", J. Amer. Chem. Soc. 120(1):7–11 (1998).
Drueckhammer, "New approaches to fluorescence based glucose sensors", Database FEDRIP on Dialog, NTIS, 00313296, Identifying No. 1R21DK55234–01, Abstract (1998).
Rao, "Protein engineered glucose sensor", Database FEDRIP on Dialog, NTIS, 00352410, Identifying No. 1R01RR14170–01, Abstract (1998).
Careaga et al, "Large Amplitude Twisting Motions of an Interdomain Hinge: A Disulfide Trapping Study of the Galactose–Glucose Binding Protein", Biochemistry 34:3048–3055 (1995).
Vyas et al, "Crystallographic Analysis of the Epimeric and Anomeric Specificity of the Periplasmic Transport/Chemosensory Protein Receptor for D–Glucose and D–Galactose", Biochemistry 33:4762–4768 (1994).
Rougier et al, "Use of Lectin To Detect The Sugar Components of Maize Root Cap Slime", J. Histochem Cytochem 27(4):878–881 (1979)—Abstract Biosis No.: 000068056576.
Boos et al, "Transport Properties of the Galactose–binding Protein of *Escherichia coli*", The Journal of Biological Chemistry 247(3):917–924 (1972).

*Primary Examiner*—Christopher L. Chin
(74) *Attorney, Agent, or Firm*—Nixon & Vanderhye P.C.

(57) ABSTRACT

The present invention relates to a glucose biosensor comprising a genetically engineered Glucose Binding Protein (GBP). In a specific embodiment, the invention relates to a GBP engineered to include mutations that allow site specific introduction of environmentally sensitive reporter groups. The signal of these prosthetic groups changes linearly with the degree of glucose binding. Thus, the glucose sensor of the invention can be used, for example, for detection of glucose in blood or industrial fermentation processes.

6 Claims, 4 Drawing Sheets

*Construction of a Novel Glucose Sensor*

*Blue LED-based fluorometer.*

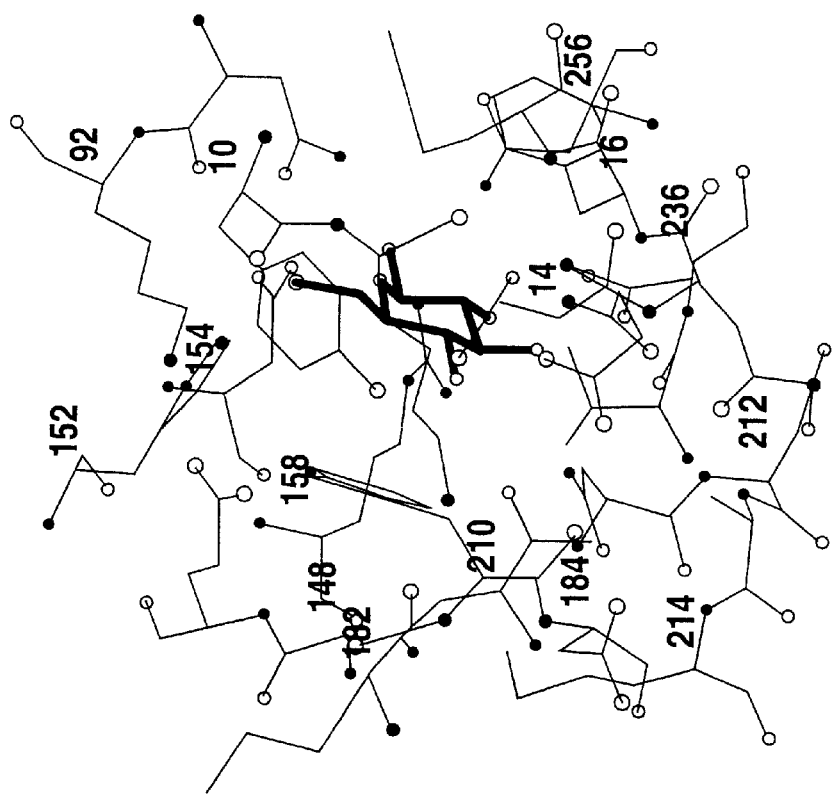
Fig. 4
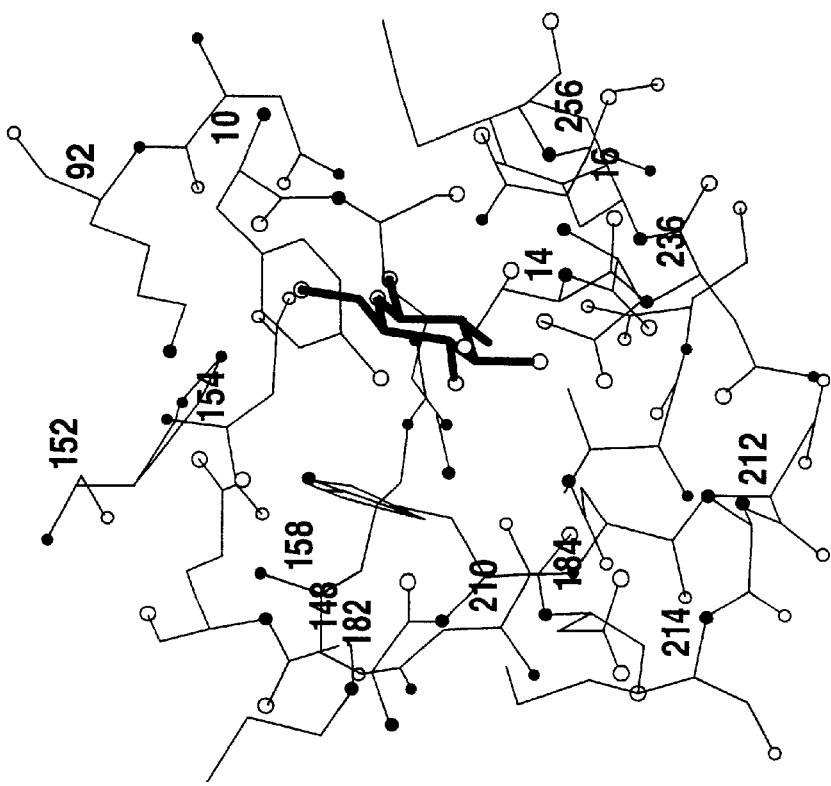

BIOSENSOR

This application is a division of application Ser. No.09/223,775, filed Dec. 31, 1998 now U.S. Pat. No. 6,277,627, the entire content of which is hereby incorporated by reference in this application.

This application claims priority from Provisional Application 60/070,293, filed Dec. 31, 1997, the entire contents of that application being incorporated herein by reference.

TECHNICAL FIELD

The present invention relates, in general, to biosensors and, in particular, to a glucose biosensor comprising a genetically engineered Glucose Binding Protein.

BACKGROUND

Biosensors couple highly specific biomolecular ligand binding events to changes in physical signals, thereby providing analytical tools that can measure the presence of single molecular species in complex mixtures. (Hall, Biosensors, Prentice-Hall: Englewood Cliffs (1991)). Most biosensors are naturally occurring macromolecules, such as enzymes or antibodies, which provide the desired analyte specificity, but often are not well suited to simple signal transduction mechanisms. (Griffiths et al, Tr. Biotech. 11:122–130 (1993)). One solution to this problem is to use protein engineering techniques to integrate signal transduction functions directly into proteins, adapting them to straightforward detection technologies, rather than developing instrumentation specific to the properties of a particular protein (Adams et al, Nature 39:694–697 (1991); Braha et al, Chem. Biol. 4:497–505 (1997); Brennan et al, Proc. Natl. Acad. Sci. U.S.A. 92:5783–5787 (1995); Brune et al, Biochemistry 33:8262–8271 (1994); Cornell et al, Nature 387:580–583 (1997); Gilardi et al, Anal. Chem. 66:3840–3847 (1994); Godwin et al, J. Am. Chem. Soc. 118:6514–6515 (1996); Marvin et al, Proc. Natl. Acad. Sci. U.S.A. 94:4366–4371 (1997); Post et al, J. Biol. Chem. 269:12880–12887 (1994); Romoser, J. Biol. Chem. 272:13270–13274 (1997); Stewart et al, J. Am. Chem. Soc. 116:415–416 (1994); Thompson et al, J. Biomed. Op. 1:131–137 (1996); Walkup et al, J. Am. Chem. Soc. 119:5445–5450 (1997)). A simple approach to building such integrated signal transducers is to exploit optical detection strategies based on changes in fluorescent reporter groups which respond to ligand binding (Guiliano et al, Annu. Rev. Biophys. Biomolec. Struct. 24:405–434 (1995); Czarnik, Chem. Biol. 2:432–438 (1995)). Fluorophores can be site-specifically introduced into a protein by using total synthesis, semi synthesis, or gene fusions. In this way pairs of fluorophores can be arranged for detection of binding by fluorescence energy transfer, or a single, environmentally-sensitive fluorophore can be positioned to respond to conformational changes accompanying binding events. (See references cited above.)

Ideally, the structural relationship between ligand binding site and reporter group is such that each can be manipulated independently, allowing a modular approach to the optimization of the properties of the binding site or the fluorophore. (Marvin et al, Proc. Natl. Acad. Sci. U.S.A. 94:4366–4371 (1997); Walkup et al, J. Am. Chem. Soc. 119:3443–3450 (1997); Cheng et al, J. Am. Chem. Soc. 118:11349–11356 (1996); Ippolito et al, Proc. Natl. Acad. Sci. U.S.A. 92:5017–5021 (1995); Elbaum et al, J. Am. Chem. Soc. 118:8381–8387 (1996)). One way to achieve such modularity is to spatially separate the two sites to minimize steric interference between them. Spatial separation of the reporter group and the binding site requires that the behavior of the fluorophore remain coupled to the degree of occupancy of the ligand binding site via an allosteric linkage mechanismn. Recently, it has been shown that it is possible to engineer such integrated fluorescent allosteric signal transducer (FAST) functions in the Maltose Binding Protein (MBP) of E. coli by taking advantage of the large conformational changes that occur upon ligand binding in this protein, using a structure-based rational design approach (Marvin et al, Proc. Natl. Acad. Sci. U.S.A. 94:4366–4371 (1997)).

The present invention relates, in one embodiment, to a Glucose/Galactose Binding Protein with engineered FAST functions and to a new class of fluorescent glucose sensors with applications in the food industry (Suleiman et al, In:Biosensor Design and Application, Matthewson and Finley, Eds. American Chemical Society, Washington, D.C., Vol. 511 (1992)), and clinical chemistry (Wilkins et al, Med. Eng. Phys. 18:273–278 (1996); Pickup, Tr. Biotech. 11:285–291 (1993); Meyerhoff et al, Endricon 6:51–58 (1996)).

SUMMARY OF THE INVENTION

The present invention relates to a glucose biosensor comprising a genetically engineered Glucose Binding Protein (GBP). In a specific embodiment, the invention relates to a GBP engineered to include mutations that allow site specific introduction of environmentally sensitive reporter groups. The signal of these prosthetic groups changes linearly with the degree of glucose binding. Thus, the glucose sensor of the invention can be used, for example, for detection of glucose in blood or industrial fermentation processes.

BRIEF DESCRIPTION OF THE DRAWINGS

FIG. 4. Glucose binding pocket in GBP (Protein Databank Ref 2GBP).

DETAILED DESCRIPTION OF THE INVENTION

Figure 1:
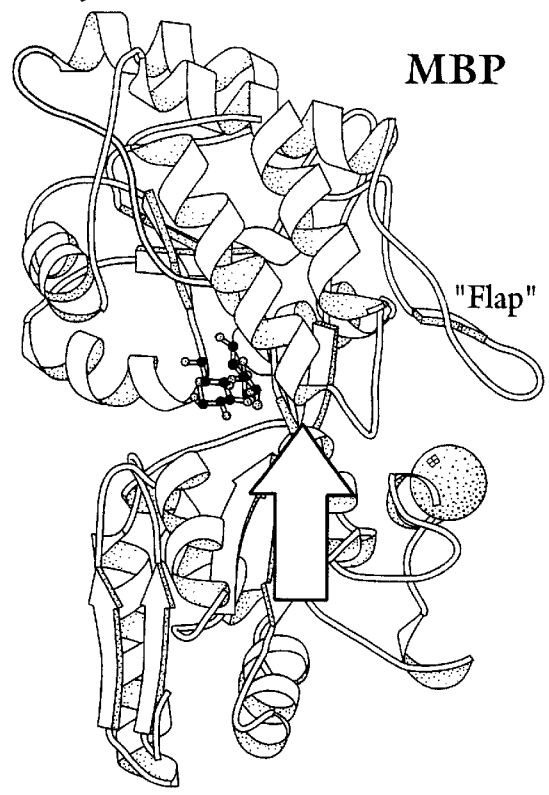
FIG. 1. Comparison of the closed forms of MBP (Spurlino et al, J. Biol. Chem. 266:5202–5219 (1991)) (top; Protein Data Bank ref 2MBP) and GBP (Vyas et al, Nature, 327:635–638 (1987); Vyas et al, Science 242:1290–1295 (1988); Vyas et al, Biochemistry 33:4762–4768 (1994)) (bottom: PDB ref IGLG) complexed with their respective substrates, showing position. Attachment sites of conjugated fluorophores are indicated by spheres. The sphere located in the "flap" region of MBP indicates the position of the fluorophore that was found to give the best allosteric response (Marvin et al Proc. Natl. Acad. Sci. USA 94:4366–4371 (1977)) (attached to Asp95Cys). On the basis of this result, four sites in the analogous region of GBP (255, 257, 294, 296) are predicted to be potentially allosterically linked to the glucose binding pocket. Sites 15 and 152, located in the glucose binding pocket, are positions for potential nonallosteric reporter groups. The ribbon diagrams were produced with Molscript (Krollis, J. Appl. Crystal. 24:946–950 (1991)).
Figure 1:
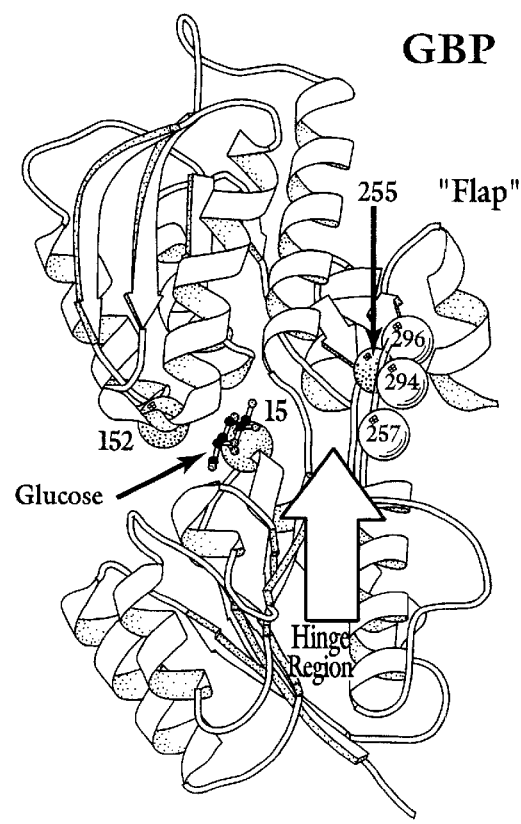

The present invention relates to a novel glucose-sensing protein engineered from GBP to include amino acid residues that allow site-specific introduction of environmentally sensitive reporter groups, such as fluorophores. The invention results, at least in part, from the identification of regions in GBP that are either placed directly within or are allosterically coupled to the glucose binding site.

Prior to the production of the glucose sensors of the invention, allosteric sites had been identified in the Maltose Binding Protein (MBP) (Marvin et al, Proc. Natl. Acad. Sci. USA 94:4366–4371 (1997)). Direct identification of the allosteric sites was possible as high resolution X-ray structures of MBP were known in both the maltose-bound ("closed") and maltose-free ("open") states. By contrast, GBP had been crystallized only in the "closed" (ie, glucose-bound) conformation and thus direct calculation of potentially allosteric site (PAS) locations was precluded. While MBP and GBP share little homology, have different molecular weights and even somewhat different secondary structure topology, it proved possible to exploit the rough structural similarity between the two proteins to predict the location of allosteric sites in GBP (Vyas et al, Nature 327:635–638 (1987); Vyas et al, Science 242:1290–1295 (1988); Vyas et al, Biochemistry 33:4762–4768 (1994)).

While glucose sensors of the invention are described in some detail in the Examples that follow, it will be appreciated that the particular engineered GBP's described represent only individual embodiments. Further, it will be appreciated that as GBP is a member of a superfamily of receptor proteins, the invention includes engineered GBP's other than engineered *E. Coli* GBP's, such as engineered thermophilic bacteria GBP (see Tam et al, Microbiol. Rev. 57:320 (1993)).

Engineered proteins of the invention can be produced by site-specifically introducing a reporter group(s) by total synthesis, semi synthesis, or gene fusions (see Godwin et al (1996), Walkup et al (1997), Adams et al (1991), Brune et al (1994), Gilardi et al (1994), Marvin et al (1997), Post et al (1994), Thompson et al (1996), Romoser et al (1997), all cited above)).

A variety of reporter groups can be used, differing in the physical nature of signal transduction (e.g., fluorescence, electrochemical, nuclear magnetic resonance (NMR), and electron paramagnetic resonance (EPR)) and in the chemical nature of the reporter group. For example, a variety of different fluorophores can be used. Fluorophores that operate at long excitation and emission wavelengths (e.g., >600 nm) are preferred when the molecular sensor is to be incorporated into a transdermal biosensor (the skin being opaque below 600 nm). Presently, there are few environmentally sensitive probes available in this region of the spectrum and none with thiol-reactive functional groups (Thompson, R. B., Red and near-infrared fluorometry, in Topics in Fluorescence Spectroscopy, J. R. Lackowicz, Editor 1994, Plenum Press: New York, p. 151–181). However, thiol-reactive derivatives of osmium(II) bisbipyridyl complexes and of the dye Nile Blue can be prepared (Geren et al, Biochem. 30:9450 (1991)). Conjugates containing these fluorophores, for example, attached at various cysteine mutants constructed in the hinge region of GBP, can be screened to identify which results in the largest change in fluorescence upon glucose binding. Os(II) bisbipyridyl complexes have absorbances at wavelengths longer than 600 nm with emission maxima in the 700 to 800 nm region (Demas et al, Anal. Chem. 63:829A (1991)) and the life-times are long (in 100 nsec range), simplifying the fluorescence lifetime instrumentation. The absorbance and luminescence properties of these complexes can be tuned readily by ligand substitution. In these complexes, Os toxicity is reduced because the Os(II) state is exchange inert (greatly reducing any potential loss of metal from the complex), and the redox potential~1 V so that it is unlikely to be oxidized to OS(III) under physiological conditions (Demas et al, Anal. Chem. 63:829A (1991)). Redox cofactors can also be used as reporter groups, e.g., ferrocene and thiol-reactive derivatives thereof. Thiol-reactive derivatives of organic free radicals such as 2,2,6,6-tetramethyl-1-piperinoxidy (TEMPO) and 2,2,5,5-tetramethyl-1-piperidinyloxy (PROXYL) can also be used and changes in the EPR spectra of these probes in response to ligand binding monitored.

The reporter group(s) can be positioned in the binding pocket of the GBP (Vyas et al, Nature 327:635–638 (1987); Vyas et al, Science 242:1290–1295 (1988); Vyas et al, Biochemistry 33:4762–4768 (1994)), so that changes in reporter signal are a consequence of direct interactions with the bound glucose. This approach may be disadvantageous in that it can be accompanied by unfavorable steric interactions between the reporter group and glucose which lower the glucose affinity or substrate selectivity. Alternatively, the reporter group(s) can be positioned in locations distant from the binding site where the reporter group(s) senses glucose binding indirectly via an allosteric coupling mechanism based on detection of the domain movements. Appropriate allosteric sites are located in regions of GBP that undergo a local conformational change in concert with the interdomain bending motion. In the case of MBP, the positions of such sites were deduced by comparison of the experimentally determined structures of both protein conformations (ie, "open" and "closed"). As indicated above, it proved possible to extend this analysis to GBP on the basis of the rough structural homology between the two proteins. The allosteric sensing mechanism has the advantage that there is no direct interaction between the reporter group and glucose, so that the original properties of the binding site are essentially unaffected. The allosteric design strategy is modular in nature, that is, the ligand-binding site can be altered without destroying the reporting properties of the attached reporter, and vice versa.

In a further aspect of the present invention, mutations are introduced both at an allosteric site (for purposes of reporter group linkage) and in the binding site in order to alter affinity of the protein for glucose without destroying, or unduly impacting, allosteric linkage with the reporter group. This aspect of the invention can find application, for example, when the biosensor is used for determining blood glucose concentrations. Blood glucose is typically about 7 mM and fluctuates between 5–15 mM in diabetic conditions (Tietz Textbook of Clinical Chemistry, $2^{nd}$ ed., (1986) Burtis and Ashwood (eds.) Saunders, London). In order to accurately determine the glucose concentration without the necessity for sample dilution, the binding constant of the engineered biosensor be adjusted so as to match the physiological (and pathological) operating range. Wild type GBP has a $K_d$ (glucose)=0.8 μm. Advantageously, a biosensor of the invention has a weaker binding constant (about four orders of magnitude weaker) but is still specific for glucose. For example, biosensors having a binding constant for glucose in the range of 0.8 µM to 20 mM can be used. Advantageously, the binding constant is in the range of 1 mM to 20 mM when the biosensor is to be used for clinical purposes. Binding constants can be determined, for example, by measuring the fluorescence change of an engineered protein in response to known quantities of glucose (see Examples that follow). Similarly, binding constants can be "tuned" to match the operating conditions in industrial processes.

Mutations that change the binding constant of GBP without altering the sugar specificity can be identified by examination of the three-dimensional structure of the glucose binding pocket in GBP (FIG. 4). Three categories of interactions between the protein and the bound sugar can be altered: (A) direct hydrogen bond interactions, (B) direct van der Waals interactions, (C) indirect van der Waals or hydrogen-bond contacts. Class (A) contacts are most likely to contribute to specificity and therefore may be left unaltered. Class (B) and (C) contacts can be altered by site-directed mutagenesis with specific residues being mutated, in the first instance, to alanine. W183A and Y10A single mutants, as well as the W183AY10A double mutant, have been constructed in an allosterically signaling construct designated 255C. These mutations change the binding constant for glucose from 0.2 µM to 20 µM, 50 µM and 650 µM, respectively, demonstrating that the binding constant can be "tuned" without destroying the allosteric signaling mechanism. The D154AW183A double mutant described in Example 5 (also in a 255C background) has a binding constant of 7.2. Other mutations involving, for examples Phe16, Lys92, Glu147, Lys9, Asp184, Asn14, Asn91, His152, Asp154, Arg158, Asn211, Asp236, Asn256; Tyr10, Met17, Asn66, Ser112, Ser115, Trp183, Asn210, Met214, Gln261 and/or Tyr295, can be made. In addition to changing specific positions to alanine, the effect of other amino acids can also be determined. Advantageously, all mutations will also be examined in the non-allosteric 152C background.

The biosensor of the invention can be used in essentially any setting where glucose detection is required. For example, the present biosensor can be used in the food industry (Suleiman et al, In: Biosensor Design and Application: Mathewson and Finley Eds; American Chemical Society, Washington, D.C. 1992, vol. 511) and in clinical chemistry (Wilkins et al, Med. Eng. Phys. 18:273–288 (1996); Pickup, Tr. Biotech. 11:285–291 (1993); Meyerhoff et al, Endricon 6:51–58 (1966); Riklin et al, Nature 376:672–675 (1995); Willner et al, J. Am. Chem. Soc. 118:10321–10322 (1996)). The biosensor of the invention can be used, for example, as the basis for the construction of a fluorescent flow cell containing immobilized GBP-FAST conjugates. (See Wilkins et al, Med. Eng. Phys. 18:273–288 (1966), Pickup, Tr. Biotech. 11:285–291 (1993); Meyerhoff et al, Endricon. 6:51 (1966); Group, New Engl. J. Med. 329:977–986 (1993); Gough et al, Diabetes 44:1005–1009 (1995)). The present biosensor can be used in an implantable device suitable for use as an artificial pancreas.

Certain aspects of the present invention are described in greater detail in the non-limiting Examples that follows. (See also Marvin et al, J. Am. Chem. Soc. 120:7 (1998)).

EXAMPLES

The following experimental details relate to the specific Examples that follow.

Mutagenesis. The gene for the cytoplasmic form of GBP (Scholle et al, Mol. Gen. Genet. 208:247–253 (1987)) (i.e., lacking the leader sequence peptide) was amplified from E. coli genomic DNA using the Polymerase Chain Reaction (PCR) with flanking primers designed to introduce an EcoRI restriction site 5' to the start codon N-Terminus (5' CCG GAA TTC GGA GAT ACC ATG GCT GAT ACT CGC ATT GGT GTA ACA ATC TAT 3'; restriction site and start codon are underlined), and a BamHI site just before the stop codon (5' AAG CTT TCA TTA GGA TCC TTT CTT GCT GAA CTC AGC CAG GTT GCT TTT 3'). The resulting fragment was cloned into the pKK223-3 expression vector (Pharmacia). An oligonucleotide cassette coding for a $His_5$ oligopeptide was subsequently cloned into the BamHI site to allow single-step purification by Immobilized Metal Affinity Chromatography (Hochuli et al, Bio/Technol. 6:1321–1325 (1988)) (IMAC). Individual cysteine mutants were made by overlapping PCR fragment mutagenesis.

Protein Expression and Purification. A colony of E. coli XL1blue cells (Stratagene) freshly transformed with a plasmid expressing a mutant GBP protein was grown at 37° C. overnight in 20 mL of 2XYT medium containing 100 µg/mL ampicillin. 2XYT medium (1 L) supplemented with 0.2% (w/v) glucose was inoculated with 10 mL of the overnight culture and grown with vigorous shaking at 37° C. until $OD_{600}$-0.5. Protein expression was induced with 1 mM 1PTG and grown for a further 4 h. Cells were harvested by centrifugation at 3000 g, resuspended in 40 mL of high salt buffer (1 M NaCl, 50 mM phosphate, pH 7.0; HSB), and stored frozen at −80° C. The cells were thawed and lysed in a chilled French press at 1200 psi. Cellular debris was removed by centrifugation at 6000 g for 10 min. DNA was precipitated by addition of polyenimine (pH8) to 5% (w/v) and removed by centrifugation at 6000 g for 30 min. GBP was purified with a single-step IMAC (Hochuli et al, Bio/Technol. 6:1321–1325 (1988)) procedure. Cleared lysate was diluted to 100 mL with HSB onto a 30 mL iminodiacetate/zinc column (Pharmacia) and extensively washed with HSB to remove unbound proteins (and bound glucose), followed by elution of mutant GBP with use of a 200 mL, 0–100 mM imidazole gradient in HSB. GBP was located in a single late peak that revealed only one protein band on an overloaded SDS/polyacrylamide gel stained with Coomassie Blue. Yields were typically 5 mg/L growth.

Fluorophore Coupling. Fluorophores were conjugated to the mutant GBP proteins via the single free cysteine. Acrylodan (Prendergast et al, J. Biol. Chem. 259:7541–7544 (1983)) and (((2-(iodoacetoxy)ethyl)methyl)amino)-7-nitrobenz-2-oxa-1,3-diazole (Ghosh et al, Biochem. J. 108:155 (1968)) (IANBD) were purchased from Molecular Probes and used without further purification. The fluorophores were dissolved in acetonitrile and reacted with freshly purified cysteine mutants (5:1 molar ratio) of GBP (~1 mg) in 1 M NaCl, 50 mM phosphate buffer (pH 7.0), for 3–5 h at room temperature. Unreacted fluorophore was separated from protein by gel filtration. The extent of coupling was measured both by determining the remaining free thiol concentration with use of Ellman's reagent (Ellman, Arch. Biochem. Biophy. 82:70–77 (1959)) and by using the ratio of the absorbances of the major protein and fluorophore chromophores ($\epsilon_{280}$(GBP)=37 $mM^{-1}$ $cm^{-1}$ (this study); $\epsilon_{469}$(IANBD)=23 $mM^{-1}$ $cm^{-1}$; $\epsilon_{392}$(acrylodan)=20 $mM^{-1}$ $cm^{-1}$). Coupling was always found to be greater than 95%. The conjugates were stable at 4° C. for a period of months, as determined by glucose binding assays.

Measurement of Glucose and Galactose Binding. Sugar binding was determined by measuring changes in fluorescence of the conjugated fluorophores on a SLM-Aminco-Bowman series-2 fluorimeter at 25±1° C. Glucose or galactose (Sigma) was titrated into a 50 nM conjugated protein solution in 0.1 M NaCl, 50 mM phosphate (pH 7.0), which was continuously mixed with a magnetic stirrer. For titrations, the excitation and emission slit widths were set to 4 and 16 nm, respectively (IANBD:$\lambda_{ex}$=469 nm, $\lambda_{em}$=540 nm; acrylodan: $\lambda_{ex}$=392 nm, $\lambda_{em}$=520 nm). Under these conditions the instrument noise was <1% of the fluorescence signal observed in saturating solutions of glucose. Experimentally observed binding curves were fit to a binding isotherm:

$$\Delta F = \Delta F_{max}(1+K_d/S)^{-1} \qquad (1)$$

where $\Delta F$ is the change in fluorescence, $\Delta F_{max}$ the fluorescence change at saturating concentrations of ligand, $K_d$ the binding constant, and S the concentration of ligand.

Example 1

Identification of Allosterically Linked Reporter Sites

The conformational differences of the high-resolution X-ray structures of the open (Spurlino et al, J. Biol. Chem. 266:5202–5219 (1991) and closed (Sharff et al, Biochemistry 31:10657–10663 (1992)) forms of MBP were analyzed, and regions that were predicted to be allosterically linked to the binding site were analyzed (Marvin et al, Proc. Natl. Acd. Sci. USA 94:4366–4371 (1977)). Site-specific attachment of environmentally sensitive fluorophores demonstrated that these regions are allosterically coupled to maltose binding. GBP has been crystallized only in the closed conformation, precluding direct calculation of potentially allosteric site (PAS) locations. Instead, the results obtained on MBP were used, and the rough structural similarity between MBP and GBP relied upon to predict the location of analogous PASs in the latter, even though the two proteins share little sequence homology and are of different molecular weight and somewhat different secondary structure topology (Hsiao et al, J. Mol. Biol. 262:225–242 (1996)).

The site that gave the most pronounced allosteric signaling in MBP is located in a region that forms a mobile "flap" covering the actual hinge. This flap is formed by two unconnected halves, each confined to one of the domains. Their relative movement changes the environment of an attached fluorophore which is completely separated from the binding pocket by the hing β-sheet. The equivalent flap region in GBP is much smaller, with only one-half truly retained, which limits the attached positions in GBP to the hinge itself (FIG. 1).

Faced with the limited amount of structural information available for GBP, the search for PAS locations was restricted to this region. Since it is impossible to predict which of the residues in the flap region is likely to give the most pronounced allosteric response to ligand binding, the β-sheet portion of the flap was scanned and four sites for reporter group attachment (L255, D257, P294, V296) were identified. These positions are all located in one side of the hinge β-sheet, forming a surface onto which the flap α-helix is packed. Their microenvironment is therefore predicted to change if the flap region rearranges upon ligand binding.

Example 2

Nonallosteric (Peristeric) Reporter Sites

In addition to the PAS mutations, two sites for attachment of reporter groups in the binding site itself were identified (N15, H152). Fluorophores placed in these positions are predicted to respond to changes in their microenvironment by direct interaction with the ligand, by protein conformational changes as the "jaws" of the binding site close around the ligand, or by changes in solvation. This strategy has been used successfully to introduce nonallosteric signal transducing fluorescent reporter groups in MBP (Gilardi et al, Anal. Chem. 66:3840–3847 (1994)) and Phosphate Binding. Protein (Brune et al, Biochemistry 33:8262–8271 (1994)) (PBP), another member of the periplasmic binding protein family, which binds to inorganic phosphate. In both cases the ligand binding constant of the conjugated protein is significantly increased relative to wild-type, indicating a significant degree of steric interference between the ligand and the fluorophore, which may also account for the change in the microenvironment of the fluorophore (Gilardi et al, Prot. Engin. 5:479–486 (1997)). This strategy therefore loses the steric independence between reporter group and binding site inherent in the allosteric approach.

Example 3

Signal Transduction Properties of Mutants

The six GBP variants with single cysteines introduced for site-specific covalent attachment of fluorophores were constructed by a PCR mutagenesis strategy. Table 1 shows the results of the acrylodan (Prendergast et al, J. Biol. Chem. 259:7541–7544 (1983)) or (((2-(iodoacetoxy)ethyl)methyl)amino)-7-nitrobenz-2-oxa-1,3-diazole (Ghosh et al, Biochem. J. 108:155 (1968)) (IANBD) conjugates of these mutant proteins. These two fluorophores have been selected because of their known sensitivity to the polarity of their microenvironments.

TABLE 1

Binding Properties of Fluorescent Conjugates of the Mutant Proteins

| | IANBD | | | acrylodan | | |
|---|---|---|---|---|---|---|
| mutant | R | $K_d$(Glc) $\mu$M | $K_d$(Gal) $\mu$M | R | $K_d$(Glc) $\mu$M | $K_d$(Gal) $\mu$M |
| N15C | 0.8 | 0.13 | 0.1 | 0.7 | 0.17 | 0.15 |
| H152C | 4.0 | 20 | 160 | 1.0 | nd | nd |
| L255C | 0.8 | 0.32 | 0.49 | 0.5 | 0.43 | 0.62 |
| D257C | 1.6 | 0.80 | 1.5 | 0.8 | 0.5 | 0.5 |
| P294C | 1.0 | nd | nd | 0.9 | 1 | 1 |
| V296C | 0.7 | 0.1 | 0.3 | 1.0 | nd | nd |

R: ratio of fluorescence of fully saturated GBP (10 mM glucose) to apoprotein (R = 1.0 indicates no change; R < 1.0 indictes a decrease upon glucose binding; R > indicates an increase). $K_d$(Glc), $K_d$(Gal): binding constant ($\mu$M) for glucose and galactose, respectively (nd: not done; binding constants were determined for all cases where R ≠ 1.0). Wild-type has a $K_d$(Glc) = 0.2 $\mu$M, and $K_d$(Gal) = 0.4 $\mu$M (Miller et at, J. Biol. Chem. 258: 13655–13672 (1983)). N15C and H152C are the positions for nonallosteric reporter groups, the other four mutants are located in the hinge region of the allosteric flap.

Figure 2A:
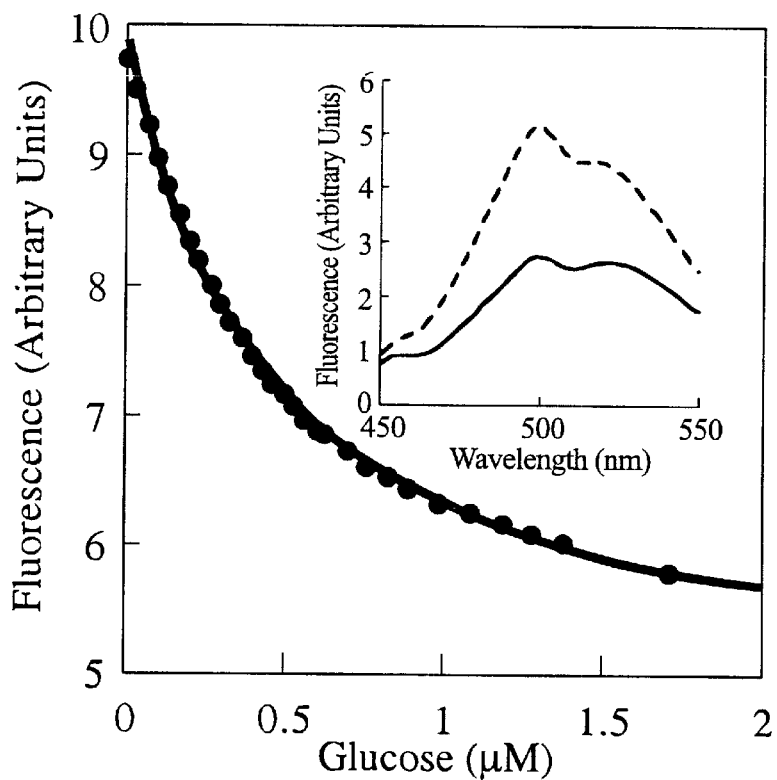
FIGS. 2A and B. Binding of glucose to the L255C-acrylodan (FIG. 2A) and H152C-IANBD (FIG. 2B) conjugates. The binding curve is the average of three separate titrations (error bars are smaller than the circles shown). Insert shows changes in the emission spectra upon addition of saturating glucose: no glucose (dashed line), 10 mM glucose (solid line).
Figure 2B:
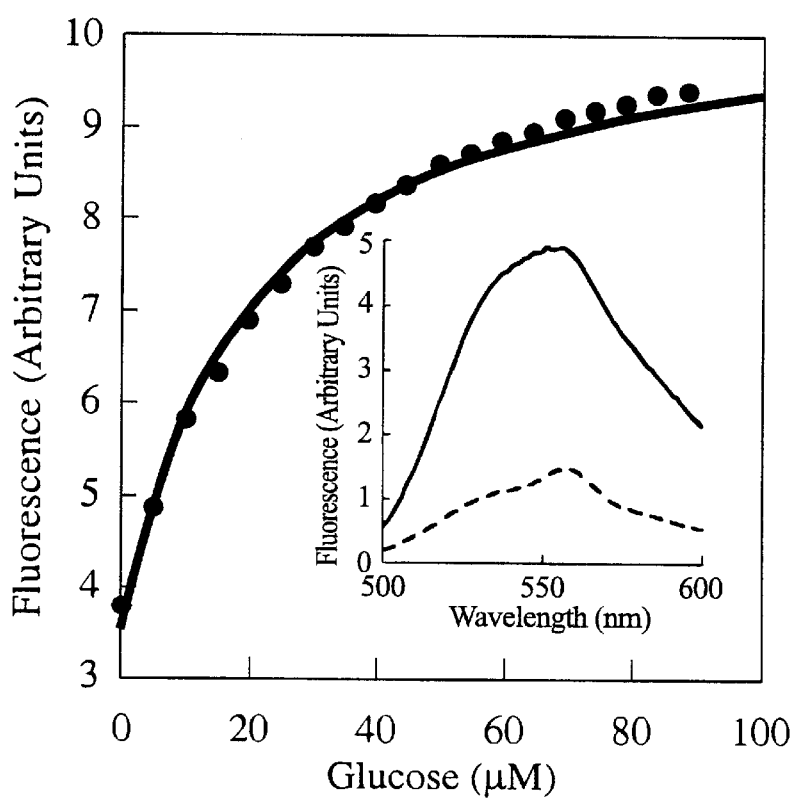

All four mutants in the hinge region showed a change in fluorescence of their acrylodan or IANBD conjugates upon ligand binding. The acrylodan conjugate at position 255 gives the largest change (2-fold decrease; FIG. 2A). In all cases, a single-site hyperbolic binding curve could be constructed by measuring the change in fluorescence as a function of glucose or galactose concentration, from which we conclude that the fluorophores attached to the hinge region are allosterically linked to the sugar binding pocket, as predicted. Furthermore, the sugar binding constants are affected by no more than a factor of 4, indicating that the FAST and ligand binding sites are sterically separated, as intended.

Two cysteine mutations were also constructed in the binding pocket itself (FIG. 1). H152C interacts directly with the sugar, since it replaces his152 which forms a hydrogen bond with the O6 oxygen of both galactose and glucose. (Vyas et al, Biochemistry 33:4762–4768 (1994)). The largest change in fluorescence of all the variants explored in this study (4-fold increase) was observed with IANBD attached at this position. However, this conjugate shows a large increase in the binding constants for glucose (~100-fold) and galactose (~500-fold) as would be expected both from the loss of the hydrogen bond to the O6 oxygen and from direct steric interference with the bound sugar.

Fluorophores attached to N15C are intended to respond to changes in the interdomain distance, rather than by direct interaction with the sugar, since Asn15 points away from the sugar binding pocket. Both the acrylodan and the IANBD conjugates show a change upon sugar binding, though not as large as IANBD at the 152 position. However, the conjugates at the 15 position do not greatly perturb the sugar binding constants, indicating that there is no direct interaction with the sugar.

Example 4

Microenvironment of the Fluorophore Conjugates

Both acrylodan and IANBD are sensitive to changes in the polarity of their microenvironment (Ghosh et al, Biochem. J. 108:155 (1968); Macgregor et al, Nature 319:70–73 (1986); Weber et al, J. Biochemistry 18:3075–3078 (1979)), which may result from changes in solvent accessibility, probe mobility, and changes in the steric interactions with the surrounding protein (or ligand, in the case of the H152C-NBD conjugate). Such microenvironmental changes may manifest themselves as differences in emission intensity as well as shifts in the wavelengths of their maxima. The emission maxima of acrylodan are known to be particularly dependent on the polarity of the environment, showing a significant blue shift in nonpolar relative to aqueous environments (Macgregor et al, Nature 319:70–73 (1986); Weber et al, Biochemistry 18:3075–3078 (1979)).

Figure 3:
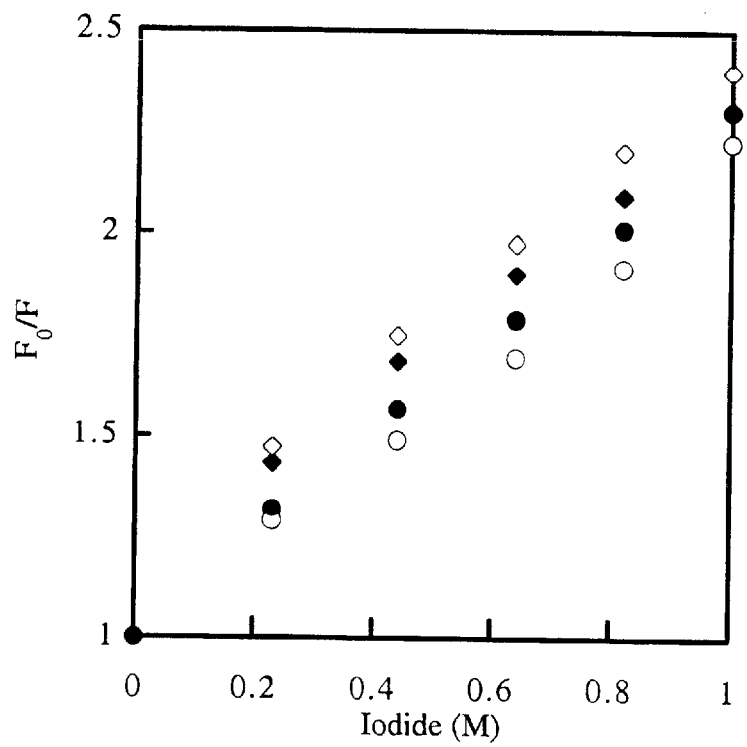
FIG. 3. Solute quenching by iodide of the L255C-acrylodan conjugate. $F_0/F$ fractional change in fluoresence emission at 498 nm upon addition of iodide. Quenching was determined for apoprotein (circles) and in the presence of 10 mM glucose (diamonds), and is plotted for both emission maxima at 498 nm (closed symbols) and 520 nm (open symbols).

The responses of the different sites vary widely. In several cases only one of the two conjugates coupled at a particular site responds to binding of the sugar (see Table 1). Furthermore, none of the conjugates show an appreciable shift in emission maxima upon ligand binding. The behavior of the best allosteric signal transducer in the hinge region, L255C-acrylodan (FIG. 3), was examined in more detail. The emission spectrum of this conjugate has two maxima (498 and 520 nm; FIG. 2A), suggesting that the attached acrylodan is present in two distinct environments differing in their polarities which are intermediate between water and ethanol based on their blue shifts relative to water (Prendergast et al, J. Biol. Chem. 259:7541–7544 (1983)). Both peaks are present in the apo and sugar-bound forms, although their relative intensity changes somewhat upon ligand binding, suggesting a slight redistribution between the two states. To examine the potential contribution of differences in the solvent accessibility of the attachment site to changes in dipolar relaxation of the fluorophore that occurs upon ligand binding, we determined the effect of iodide on the fluorescence in the presence and absence of glucose. Iodide selectively quenches solvent-exposed fluorophores. The degree of quenching follows the Stem-Volmer equation describing steady-state collisional quenching (Lehrer et al, Methods Enzymol. 49:222–236 (1978)):

$$F_0/F = 1 + K[I^-] \qquad (2)$$

where $F_0/F$ is the fractional decrease in fluorescence, and K the Stern-Volmer quenching constant (K>1.0 for a solvent-exposed fluorophore) which is related to the degree of solvent accessibility. It was found that the quenching constants measured for both emission maxima of the acrylodan are approximately the same, do not change upon glucose addition and are >1 (FIG. 3), indicating that both acrylodan conformations are partially solvent exposed, and the change in the microenvironment is unlikely to involve a change in solvent accessibility. Similar observations were made on other conjugates.

These results suggest that the mechanism by which the conformational changes affect the dipolar relaxation of the attached fluorophore does not involve change in the local solvent-accessibility of the attachment position, but is dependent on the detailed interaction of the fluorophore with its microenvironment, as was also observed for IANBD attached in the binding site of MBP (Gilardi et al, Prot. Engin. 5:479–486 (1997)).

Example 5

Alteration of Binding Constant for Glucose

Examination of the experimentally determined three-dimensional structure of GBP (see FIG. 4) indicates that there are two types of residues that form the glucose binding site, those that make direct contact with glucose through hydrogen bonds or van der Waals interactions (primary binding surface) and those that serve to orient the residues in the primary binding surface (secondary binding surface). (Primary binding surface in E. coli GBP: Asn14, Asn91, His152, Asp154, Arg158, Asn211, Asp236, Asn256; secondary binding surface in E coli GBP: Tyr10, Phe16, Met17, Asn66, Ser112, Ser115, Trp183, Asn210, Met214, Gln261, Tyr295). In order to change the binding constant for glucose, residues in both surfaces have been systematically mutated, either singly or in pairs. The data obtained are shown in Table 2. The Asp154Ala, Trp183Ala (D154A+W183A) double mutant has a binding constant of 7.2 mM. The dynamic range is thus matched for operating in physiologically relevant glucose concentration ranges.

TABLE 2

$K_d$'s of mutant proteins binding sugars (expressed in $\mu$M). NB = "non-binding"

| | Wild-type | S112A | S112A S115A | D154A | Y10A | D14A | F16Y | N91A | Y10A D154A | D154A W183A |
|---|---|---|---|---|---|---|---|---|---|---|
| D-Glucose | 0.8 | 7.2 | 9 | 11.5 | 54 | 290 | 500 | 150 | 1050 | 7200 |
| D-Galactose | 2.4 | 24.5 | 33 | 41 | 180 | 390 | 1165 | 1080 | 4400 | |
| L-Arabinose | 90 | 870 | 1100 | 2200 | 2700 | 7250 | NB | NB | | |
| D-Mannose | 105 | 670 | 1400 | 1550 | 7100 | 26000 | NB | 16000 | | |
| D-Fucose | 340 | NB | NB | 140 | NB | NB | 6000 | 1230 | NB | NB |
| Maltose | 400 | | 3300 | | NB | | NB | | | |

TABLE 2-continued

K$_d$'s of mutant proteins binding sugars (expressed in μM). NB = "non-binding"

| | Wild-type | S112A | S112A S115A | D154A | Y10A | D14A | F16Y | N91A | Y10A D154A | D154A W183A |
|---|---|---|---|---|---|---|---|---|---|---|
| Lactose | 1300 | | | | NB | | | | | |
| D-Xylose | 1400 | 4200 | | | | | | | | |
| D-Fructose | 4700 | 15000 | | 24000 | 22000 | | | | NB | |

The number refers to the sequence position in *E. coli* GBP.

Example 6

Optical Instrumentation

Figure 5:
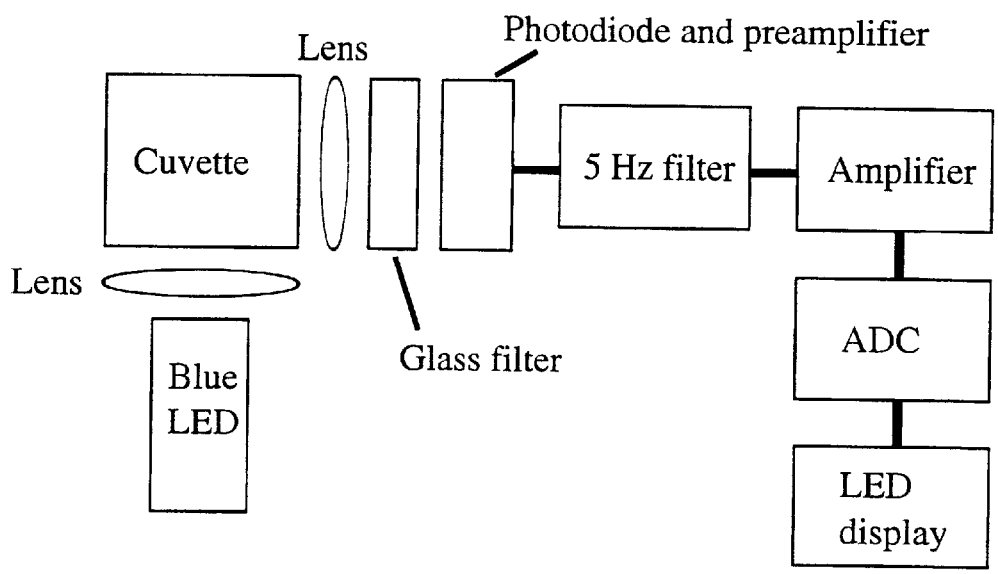
FIG. 5. Blue LED-based fluorometer.

Since the emission wavelengths of the blue LED (maximum at 470 nm, half-power±30 nm) are perfectly matched to the excitation wavelength of Nile blue dye (NBD) fluorophore (maximum at 469 nm), a simple prototype special-purpose fluorometer was constructed based on inexpensive, simple, readily available electronic components (see FIG. 5). A 1 ml cuvette is illuminated with a Nichia Chemical silicon-mixed gallium nitride blue LED (3 cd at 20 mA). A double convex lens is used to focus light into the sample. A high-pass glass filter (515 nm cutoff) is used to separate excitation from emission light. A large (100 mm$^2$) planar diffuse Si PIN photodiode (Photonic Detectors) is used to detect the emitted light. The photodiode is operated in an unbiased (photovoltaic) mode, optimized for low-noise and low-frequency operation. The signal is low-pass filtered (5 Hz cutoff), and subsequently passed through a variable summer and variable gain amplifier to achieve the desired low- and high-end calibration. LT1028 (ultra-low noise) operational amplifiers are used for all analog signal processing. A 12-bit dual-slope integrating analog-to-digital converter with a total conversion time of ~150 ms is used to average out noise from the analog input. The digital output is fed through a 27C64 EPROM. The reading appears on a four seven-segment green LED display. This instrument can detect changes in NBD fluorescence upon ligand binding to sufficient accuracy to construct a hyperbolic binding curve.

All documents cited above are hereby incorporated in their entirety by reference.

One skilled in the art will appreciate from a reading of this disclosure that various changes in form and detail can be made without departing from the true scope of the invention.

What is claimed is:

1. A method of detecting the presence of glucose in a test sample comprising
   providing a glucose biosensor comprising a glucose binding protein (GBP) and a reporter group that transduces a detectable signal, wherein said reporter group is attached to said GBP so that a signal transduced by said reporter group when said GBP is bound to glucose differs from a signal transduced by said reporter group when said GBP is not bound to glucose;
   contacting said biosensor with said test sample under conditions such that said biosensor can bind to glucose present in said test sample; and
   comparing the signal transduced by said reporter group when said biosensor is contacted with said test sample with the signal transduced by said reporter group when said biosensor is contacted with a glucose-free control sample, wherein a difference in the signal transduced by said reporter group when said biosensor is contacted with said test sample, as compared to when said biosensor is contacted with said control sample, indicates that test sample contains glucose.

2. The method according to claim 1 wherein said test sample is a physiological fluid.

3. The method according to claim 2 wherein said physiological fluid is blood, urine, interstitial fluid, or saliva.

4. A method of determining the concentration of glucose in a test sample
   providing a glucose biosensor comprising a glucose binding protein (GBP) and a reporter group that transduces a detectable signal, wherein said reporter group is attached to said GBP so that a signal transduced by said reporter group when said GBP is bound to glucose differs from a signal transduced by said reporter group when said GBP is not bound to glucose;
   contacting said biosensor with said test sample under conditions such that said biosensor can bind to glucose present in said test sample; and
   comparing the signal transduced by said reporter group when said biosensor is contacted with said test sample with a standard hyperbolic glucose binding curve prepared by measuring the signal transduced by said reporter group when said biosensor is contacted with control samples containing known quantities of glucose to determine the concentration of glucose in said test sample.

5. The method according to claim 4 wherein said test sample is a physiological fluid.

6. The method according to claim 5 wherein said physiological fluid is blood, urine, interstitial fluid, or saliva.

* * * * *